Figure 1:
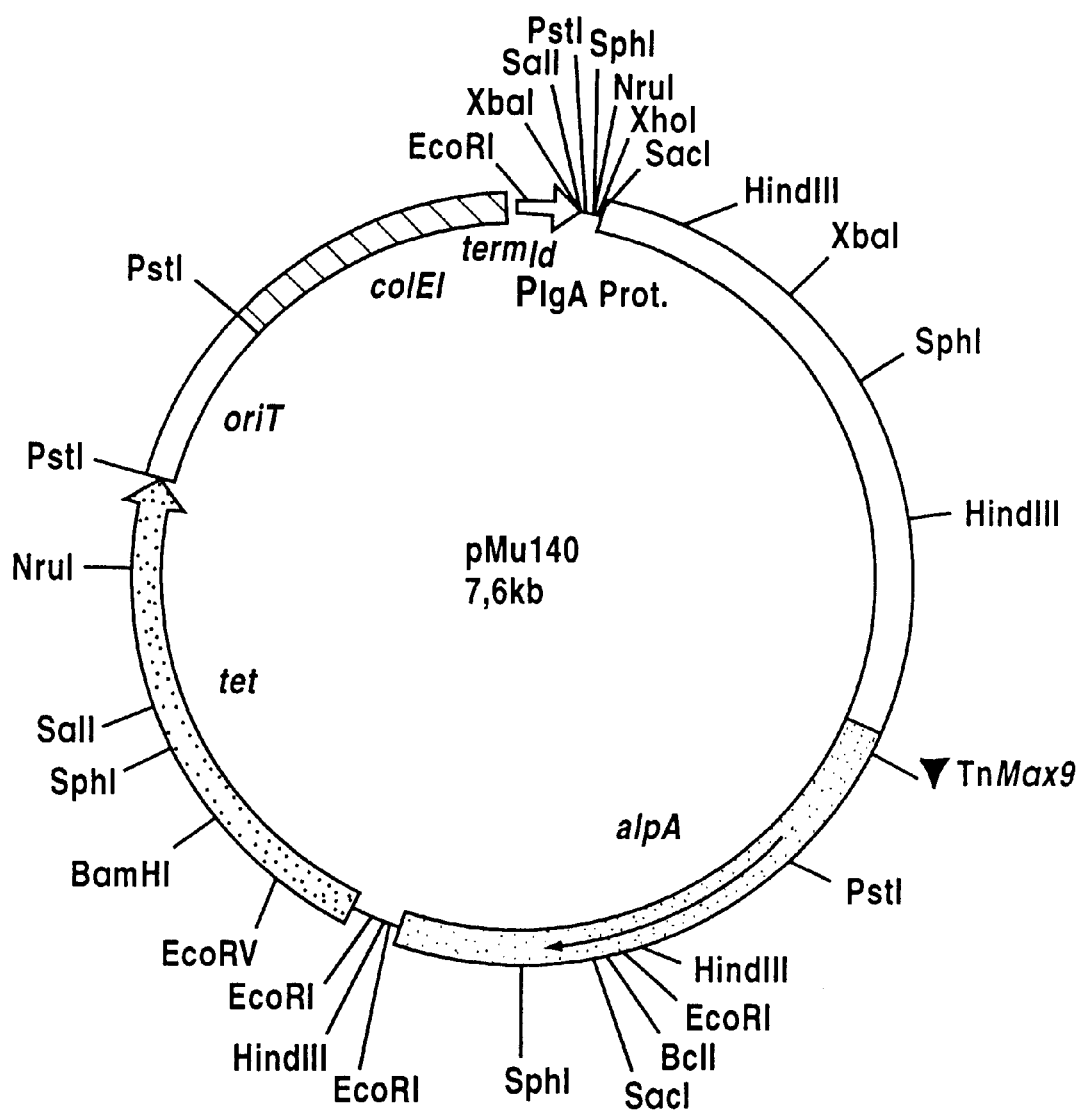

United States Patent [19]

Haas et al.

[11] Patent Number: 6,096,521

[45] Date of Patent: Aug. 1, 2000

[54] ADHESIN FROM *HELICOBACTER PYLORI*

[75] Inventors: Rainer Haas; Stefan Odenbreit, both of München; Thomas F. Meyer, Tübingen, all of Germany; André Blum, Romammôtier; Irène Corthesy-Theulaz, Lausanne, both of Switzerland

[73] Assignee: Max-Planck-Gesellschaft zur Forderung der Wissenschaften, Munich, Germany

[21] Appl. No.: 09/043,123

[22] PCT Filed: Sep. 20, 1996

[86] PCT No.: PCT/EP96/04124

§ 371 Date: Jun. 29, 1998

§ 102(e) Date: Jun. 29, 1998

[87] PCT Pub. No.: WO97/11182

PCT Pub. Date: Mar. 27, 1997

[30] Foreign Application Priority Data

Sep. 22, 1995 [DE] Germany ............................ 195 35 321

[51] Int. Cl.[7] .......................... C07H 23/02; C07H 23/04; C12N 15/00; C12P 21/04; A01N 61/00
[52] U.S. Cl. ...................... 435/70.1; 536/23.1; 536/23.7; 435/320.1; 435/71.1; 435/325; 514/1
[58] Field of Search .................................. 536/23.1, 23.7; 435/320.1, 325, 70.1, 71.1, 69.1; 514/1

[56] References Cited

U.S. PATENT DOCUMENTS 4,784,948  11/1988  Scott et al. .................................. 435/68

OTHER PUBLICATIONS

J. Biol. Chem., vol. 270, No. 17, Apr. 28, 1995, pp. 10314–10322, Sato et al., "Structure and Regulation of the Gene Encoding the Neuron–Specific Protein Kinase C Substrate Neurogranin".

J. Bacteriol., vol. 175, No. 3, Feb. 1993, pp. 647–683, Evans et al., "Cloning, Nucleotide, Sequence and Expression of a Gene Encoding an Adhesin Subunit Protein of *Helicobacter Pylori*.".

Mol. Microbio., vol. 20, No. 2, Apr. 1996, pp. 361–373, Odenbreit et al., "Optimized BlaM–Transposon Shuttle Mutagenesis of *Helicobacter Pylori* Allows the Identification of Novel Genetic . . . ".

Taussig et al., GenBank Accession No. M14958, Feb. 23, 1994.

Taussig et al., DNA, vol. 5 (6): 453–461, 1986.

Owen et al., J. Clinical Microbiology, vol. 32(5): 1203–1210, May 1994.

*Primary Examiner*—Bruce R. Campell
*Assistant Examiner*—S Chen
*Attorney, Agent, or Firm*—Arent Fox Kintner Plotkin & Kahn, PLLC

[57] ABSTRACT

The present invention concerns an adherence gene from *Helicobacter pylori*, a polypeptide coded thereby and antibodies against the polypeptide.

9 Claims, 4 Drawing Sheets

Fig.3(A)

AMINO ACID SEQUENCES COMPARISON BETWEEN AlpA AND AlpB

```
                 10         20         30         40         50
AlpA   1  MIKKNRTLFL.SLALCASISY....AEDDGGFFTVGYQLGQVMQDVQNPG  45
          |.....:. ||  .|.|. |:|:       ||:||||:|.||:|||| :|:|.|||
AlpB   1  MTQSQKVRFLAPLSLALSLSFNPVGAEEDGGFMTFGYELGQVVQQVKNPG  50

46  GAKSDELARELNADVTN NILNNNTGGNIAGALSNAFSQYLYSLLGAYP  93
          |.:|||  ||...||   ||   ..||||:||.|:|   |   .|::   ||
      51  KIKAEELAGLLNSTTTNNTNINIAGTGGNVAGTLGNLFMNQLGNLIDLYP 100

94  TKLNGSDVSANALLSGAVGSGTCAAAGTAGGTSLNTQSTCTVAGYYWLPS 143
          | ||.|.:: .  :  .:: :|:..:||..|:.||  |..:     :.|:
     101  T LNTSNITQCGTTNSGSSSSGGGAATAAATTS NKPCFQGNLDLYRKMV 148

144  LTDRILSTIGSQTNY GTNTNFPNMQQQLTYLNAGNVFFNAMNKALENK 191
          . :.||    |..  :    ..||. .|:  .||.  ||..:.|::.   ||  .: |
     149  DSIKTLSQNISKNIFQGNNNTTSQNLSNQLSELNTASVYLTYMN SFLNA 197

192  NGTSSASGTSGATGSDGQTYSTQAIQYLQGQQNIL......NNAANLLKQ 235
          |.  .::       ......|...|.|.|.|:   |..|      ||.    ||.
     198  NNQAGGIFQNNTNQAYGNGVTAQQIAYILKQASITMGPSGDSGAAAAFLD 247

236  DELLLEAFNSAVAANIGNKEFNSAAFTGLVQGIIDQSQAVYNELTKNTIS 285
          ..|  ..||||  |:|    :::..  ||:|||.|::.||....  ....||
     248  AALAQHVFNSANAGN....DLSAKEFTSLVQNIVNNSQNALTLANNANIS 293

286  GSAVISAGINSNQANAVQGRASQLPNALYNAQVTLDKINALNNQVRSMPY 335
          .|....       |  .:|  |:|..||    | |.   ||.|:.||||:::.   |:
     294  NSTGYQV...SYGGNIDQARSTQL...LNNTTNTLAKVSALNNELKANPW 337

336  LPQFRAGNSRSTNILNGFYTKIGYKQFFGKKRNIGLRYYGFFSYNGASVG 385
          |..|  ||||. .|  :|||.|||||||||||..:  |:||||||||||||||  :||
     338  LGNFAAGNSSQVNAFNGFITKIGYKQFFGENKNVGLRYYGFFSYNGAGVG 387

386  FRSTQNNVGLYTYGVGTDVLYNIFSRSYQNRSVDMGFFSGIQLAGETFQS 435
          .|  |.|.|.||||||||||:||||:..||::   |||:|||||||:|  |
     388  NGPTYNQVNLLTYGVGTDVLYNVFSRSFGSRSLNAGFFGGIQLAGDTYIS 437

436  TLRDDPNVKLHGKINNTHFQFLFDFGMRMNFGKLDGKSNRHNQHTVEFGV 485
          |||:..  .|  :::  ..|.|||||| |.|: |||||   |. .||||.:|:||
     438  TLRNSS..QLASRPTATKFQFLFDVGLRMNFGILKKDLKSHNQHSIEIGV 485

486  VVPTIYNTYYKSAGTTVKYFRPYSVYWSYGYSF 518      61% similarity
          :||||||||:|..||||||||||||| |||.|
     486  QIPTIYNTYYKAGGAEVKYFRPYSVYWVYGYAF 518      47% identity
```

Fig.3(B)

```
              10          20          30          40          50
AlpA 341 AGNSRSTNIL NGFYTKIGYK QFFGKKRNIG LRYYGFFSYN GASVGFRSTQ 390
         ||||  |  :||| ||||||||||  .:|:||||||||||||:||   .|
AlpB 343 AGNSSQVNAF NGFITKIGYK QFFGENKNVG LRYYGFFSYN GAGVGNGPTY 392

391 NNVGLYTYGV GTDVLYNIFS RSYQNRSVDM GFFSGIQLAG ETFQSTLRDD 440
         |.|.|.|||| ||||||| |:|||:..||:: |||:|||||:| ||||:.
     393 NQVNLLTYGV GTDVLYNVFS RSFGSRSLNA GFFGGIQLAG DTYISTLRNS 442

441 PNVKLHGKIN NTHFQFLFDF GMRMNFGKLD GKSNRHNQHT VEFGVVVPTI 490
          .| ::  ..|.||||||.|:||||| |..   .||||.:|: || :|||
     443 S..QLASRPT ATKFQFLFDV GLRMNFGILK KDLKSHNQHS EIGVQIPTI 490

491 YNTYYKSAGT TVKYFRPYSV YWSYGYSF 518        77% similarity
         ||||||.:|..|||||||||| |||·|
     491 YNTYYKAGGA EVKYFRPYSV YWVYGYAF 518        66% identity
```

ADHESIN FROM *HELICOBACTER PYLORI*

DESCRIPTION

The present invention concerns the new adherence gene alpB from *Helicobacter pylori* and the polypeptide coded thereby. The gene, the polypeptide and an antibody directed against the polypeptide can be used to diagnose, prevent and treat a Helicobacter infection.

The occurrence of spiral bacteria in the human gastric mucous membrane has been known for a long time (Bizzozero, 1893). The fact that these are pathogenic germs was, however, not realised until the successful isolation and culture of this bacterium by Marshall and Warren (Warren and Marshall, 1983; Marshall et al., 1984) from the gastric mucous membrane of a patient with a gastric ulcer (ulcus ventriculi). As the first analyses showed the isolated microorganisms were gram-negative, spiral bacteria with an extremely high motility and the unusual ability of being able to survive in a strongly acidic environment (up to ca. pH 1.5). The germs which were originally denoted *Campylobacter pylori* were finally classified on the basis of biochemical and morphological characteristics in the newly established genus "Helicobacter" (Goodwin et al., 1989).

The importance of *Helicobacter pylori* infection and the implications of this discovery already became clear within a few years. Epidemiological investigations by Taylor and Blaser (1991) showed that the *H. pylori* infection occurs world-wide and that ca. 50% of the population are infected with this bacterium, the infection rate being higher in the developing countries than in industrialised countries. Furthermore it was observed that the probability of a chronic *H. pylori* infection increases drastically with increasing age. Hence the *H. pylori* infection is among the most frequent chronic bacterial infections of humans.

Today it is known that the infection inevitably leads to the induction of a bacterial gastritis (type B gastritis) in humans. Moreover it is assumed that H. pylori also plays a causal role in the development of gastric and duodenal ulcers (ulcus ventriculi and ulcus duodeni) as well as some forms of gastric carcinoma (adenocarcinoma) (Lee et al., 1993; Solnick and Tompkins, 1993). Even the MALT (mucosa associated lymphoid tissue) lymphomas of the stomach which occur more rarely and are regarded as precursors of B cell tumours of the immune system are also presumably a result of *H. pylori* infection. An antibacterial treatment of such patients with the successful eradication (total elimination) of *H. pylori* leads to a healing of gastric ulcers as well as of low grade MALT lymphomas (Sipponen and Hyvärinen, 1993; Isaacson and Spencer, 1993; Stolte and Eidt, 1993).

A sequel of a long-term infection with *H. pylori* is atrophic gastritis, a degeneration of the mucous, acid or pepsin-producing cells of the stomach epithelium which has to be regarded as a pre-cancerous lesion. According to a statistic of the types of cancer which occurred world-wide most frequently in 1980, gastric carcinoma is in second place but with a declining tendency (Parkin et al., 1988). Two studies have recently shown a statistically significant correlation between *H. pylori* infection and the occurrence of gastric carcinoma (intestinal type); both came to the conclusion that ca. 60% of all gastric carcinomas that occur are probably due to a *H. pylori* infection (Parsonnet et al., 1991; Nomura et al., 1991). Furthermore investigations by Sipponen (1992) show that in many industrialised countries more than 20% of infected persons contract an ulcer of the stomach or of the duodenum during their life whereas this risk is negligibly small in persons with a normal gastric mucosa. This means that these frequent gastro-duodenal diseases must be regarded as infectious diseases and treated appropriately (Alper, 1993). A treatment which eliminates a chronic *H. pylori* infection that is already present leads to a healing of a gastritis, a gastric or duodenal ulcer or a MALT lymphoma. Thus a prophylactic treatment which prevents a *H. pylori* infection (e.g. immunization) as well as a treatment which eliminates a *H. pylori* infection that is already present can be used to treat these frequent gastro-duodenal diseases.

Apart from some higher primates, humans were previously the only known natural host for *H. pylori*. The relatively recent discovery that the domestic cat can also be infected with *H. pylori* throws new light onto the question of transmission and a possible reservoir for these bacteria outside the human organism. The occasionally successful culture of *H. pylori* from the faeces of infected persons and the ability of the bacteria to survive for months in water support the hypothesis of a faecal-oral transmission. Also direct oral-oral transmission is regarded as probable on the basis of family studies. The infection usually occurs in childhood within the family, cramped living conditions and a poor standard of hygiene correlating positively with the frequency of the infection.

After oral uptake the bacteria first reach the extremely acid stomach lumen (pH 1–2). Here the survival of the bacteria is made possible by the production of the enzyme urease which leads to cleavage of the urea that is present and thus to a local neutralization of the acidic pH value in the stomach. By means of chemotactic orientation and flagella-dependent motility the microorganisms then move into the bicarbonate-buffered mucosal layer of the antrum region of the stomach which is in fact their natural habitat. Here they are in a unique ecological niche which, due to the acid barrier, is accessible only to a few competing bacterial species. The microorganisms presumably orientate themselves by means of the pH gradient between the lumen (pH 1–2) and epithelial cell surface (pH 6–7) in order to reach the epithelium. Due to their spiral shape, their motility in viscous mucous, the production of mucous-modifying enzymes and finally their microaerophilic way of living, these germs are optimally adapted to the living conditions in this habitat.

They usually spend their time in the deep crypts of the antrum region where they are protected from external influences such as e.g. acid, pepsin and also from medicines for their eradication such as e.g. antibiotics. Part of the population (ca. 20%) is closely associated with epithelial cells especially with mucous-producing cells. Under the condition of a gastral metaplasia i.e. the acid-induced formation of gastral epithelium in the duodenum, the metaplastic areas in the duodenum are also colonised which creates the prerequisites for the development of a duodenal ulcer (ulcus duodeni). A complete excretion of the Helicobacter with the shed mucous is probably prevented by their ability to adhere so that the bacteria can persist for years, decades or even for a life time (chronic infection).

Before the existence and the significance of *H. pylori* for ulcerous diseases was known, these were treated with so-called antacids or $H_2$-receptor antagonists. These are substances which inhibit the acid secretion of the parietal cells of the stomach. The action of these pharmaceutical agents usually leads to a healing of the ulcers but, since one of the causes of these ulcers i.e. *H. pylori* infection, is not eliminated by this, in most cases a re-occurrence of the ulceration (relapse) occurs after a short time period.

A further frequently used therapy in ulcerations is bismuth treatment. Various bismuth salts (CBS, BSS) have a bactericidal effect on *H. pylori*. However, a total eradication of these germs is only achieved in 8–32% of the cases. The treatment apparently leads to a temporary suppression of the germs but after discontinuing the treatment the infection flares up again in most cases. A long-term therapy with high doses leads to an accumulation of the substance in the liver, kidney and nervous system and has considerable neurological side-effects (Malfertheiner, 1994).

Since it has been discovered that gastroduodenal ulcer diseases are infectious diseases, one aim of treatment is to eradicate the pathogens by antibiotics. Monotherapy with various antibiotics (amoxicillin, nitrofuran, furazolidin, erythromycin a.o.) has, however, turned out not to be satisfactory since even in this case eradication of the germs only occurs in 0–15% of the cases. The most successful treatment is at present achieved by a combination of an acid blocker (Ompeprazol) with an antibiotic (Amoxicillin) which can lead to eradication rates of up to 80% (Malfertheiner, 1994). However, antibiotic treatment to eliminate *H. pylori* is not promising as a long-term solution since it has to be assumed that the bacteria will rapidly develop resistance to the antibiotics.

There is therefore a need for new forms of therapy to control a *H. pylori* infection and in particular for vaccines which are specifically directed against virulence factors of *H. pylori*. Virulence factors denote the properties of a pathogenic bacterium which enable it to colonise a particular ecological niche in the body of the host and to multiply there despite the immune response and the unspecific defence mechanisms of the host organism. Knowledge about virulence factors therefore aids in the better understanding of the course and mechanisms of an infectious disease. The most important previously examined virulence factors of *H. pylori* are urease, the flagella, the adhesins and the production of a cytotoxin.

Urease, an enzyme on the surface of the bacteria is composed of two subunits (UreA, 26 kDa, UreB, 66 kDa) which constitute up to 5% of the entire bacterial protein. Urease cleaves the urea which occurs in small concentrations in gastric juice into ammonia and carbon dioxide. According to the current perception the bacterium surrounds itself with a cloud of ammonia which leads to a local neutralization of the acid of the gastric juice. The extremely high motility of the bacteria can be attributed to the presence of polar flagella which enable the bacterium to move in the viscous mucous of the gastric mucous membrane and thus to reach the epithelial cell layer. The urease gene cluster (ureA–ureH) as well as the genes for the formation of the flagella (flaA, flaB) were cloned in *E. coli* and sequenced and isogenic mutants were constructed.

Approximately 50–60% of all isolated *H. pylori* strains produce an 87 kDa protein, the so-called vacuolising cytotoxin, which induces the formation of cytoplasmic vacuoles in in vitro cell cultures. The vacA gene which codes for the cytotoxin of *H. pylori* has also been cloned in the meantime and genetically characterized. Furthermore it is presumed that the cytotoxin-producing strains have a higher pathogenic potential than strains which do not produce this toxin. In addition a positive correlation was found between the production of the cytotoxin and the development of gastric ulcers.

Investigations on the adherence of *H. pylori* to epithelial cell lines in vitro show that the bacteria can bind to many cell lines of different tissues. In contrast *H. pylori* exhibits a very pronounced species and tissue selective adherence (tropism) in the host organism. Thus the bacteria are found only bound to epithelial cells which are of the gastral type of epithelial cells. This selectivity is explained by a specific interaction between a bacterial adhesin and a specific cellular receptor.

Up to now several potential adhesins of *H. pylori* have been described and a gene (hpaA) which codes for a so-called N-acetylneuraminyllactose-binding haemagglutinin was cloned and sequenced (Evans et al., 1993). This is a protein which is supposed to recognize a receptor containing sialic acid on the epithelial cells. The significance of this adhesin for *H. pylori* infection is, however, controversial. Other potential adhesins are either only characterized by their molecular weight or their receptor binding specificity. These include a 63 kDa protein which appears to be homologous to the exoenzyme S of *Pseudomonas aeruginosa* an adhesin with ADP-ribosyl-transferase activity. Furthermore it is suspected that there is a yet unidentified adhesin which mediates a specific binding to the Lewis$^b$ blood group antigen of gastric epithelial cells (Falk et al., 1993; Borén et al., 1993).

Infection with *H. pylori* leads to a chronic inflammatory reaction of the gastric mucosa (gastritis). In addition a specific systemic immune response to *H. pylori* antigens is induced; the formation of secretory antibodies in the stomach (sIgA) has, however, not yet been indisputably clarified. As a result of the inflammation various immune cells are present in the gastric mucosa and submucosa e.g. polymorphonuclear leucocytes, monocytes, macrophages, lymphocytes and plasma cells (Blaser, 1992). In addition *H. pylori* activates neutrophils as well as monocytes and macrophages in vitro (Mai et al., 1991). Experiments with specific antibodies and complement show a rapid inactivation of *H. pylori* by neutrophils in vitro. However, in the in vivo situation these mechanisms do not lead to an inactivation of the pathogenic bacteria. How *H. pylori* survives for a long period in the host although it activates the aforementioned defence mechanism is unclear.

The host is not able to cope with the *H. pylori* infection under natural conditions. It was therefore even more surprising that the urease, an essential virulence factor of *H. pylori* (see above), has great potential as a vaccine (US Patent Application U.S. Ser. No. 07/970,996 Urease-based vaccine against Helicobacter Infection).

In the *Helicobacter felis*/mouse model (*H. felis* is a Helicobacter species which naturally colonises the stomach of the cat and can also infect the mouse) it was possible to show that oral vaccination of the *H. pylori* urease or the recombinant urease B subunit (rUreB) can protect mice against *H. felis* infection (preventive vaccine) and can also eliminate an infection which is already present (therapeutic vaccine) (Michetti et al., 1994; Corthesy-Theulaz et al., Gastroenterol., in the press). A decisive factor in the oral vaccination was the use of adjuvants such as e.g. cholera toxin which among others appears to be important for converting the immune reaction from the production of systemic antibodies to secretory antibodies.

The object of the present invention was to provide new secretory genes from *Helicobacter pylori* and polypeptides coded thereby which are potential candidates for vaccines.

In the German Patent Application 195 21 312.2 a method for identifying secretory genes from *Helicobacter pylori* is described wherein a mutant gene bank of *H. pylori* is set up with the aid of a transposon and this mutant collection is analysed for defects in adherence behaviour e.g. towards human gastric epithelial cells.

In this manner it was possible to identify an adhesin gene denoted alpA and a polypeptide coded by this gene.

While cloning the region flanking alpA located downstream a new adhesin gene from *H. pylori* denoted alpB having the nucleotide sequence shown in SEQ ID NO.1 and a polypeptide coded by this gene having the amino acid sequence shown in SEQ ID NO. 1 and 2 were identified.

Thus a subject matter of the present invention is a DNA molecule which comprises (a) the nucleotide sequence shown in SEQ ID NO.1

(b) a nucleotide sequence which corresponds to the sequence according to (a) within the scope of the degeneracy of the genetic code or (c) a nucleotide sequence which hybridizes with the sequences according to (a) or/and (b) under stringent conditions.

In addition to the nucleotide sequence shown in SEQ ID NO.1 and a nucleotide sequence corresponding to this sequence within the scope of the degeneracy of the genetic code, the present invention also encompasses a DNA sequence which hybridizes with one of these sequences under stringent conditions. The term "hybridization" according to the present invention is used as described by Sambrook et al (Molecular Cloning. A Laboratory Manual, Cold Spring Harbor Laboratory Press (1989), 1.101 to 1.104). According to the present invention a hybridization under stringent conditions means that a positive hybridization signal is still observed after washing for 1 hour with 1× SSC and 0.1% SDS at 55° C. preferably at 62° C. and especially preferably at 68° C., in particular for 1 hour in 0.2× SSC and 0.1% SDS at 55° C. preferably at 62° C. and especially preferably at 68° C. The present invention encompasses a nucleotide sequence hybridizing under such washing conditions with one of the nucleotide sequences shown in SEQ ID NO.1 or with a corresponding nucleotide sequence within the scope of the degeneracy of the genetic code.

The DNA molecule according to the invention preferably codes for a polypeptide having the ability to adhere to human cells in particular to human gastric epithelial cells. In addition it is preferred that the DNA molecule according to the invention has a homology at the nucleotide level of at least 70%, particularly preferably of at least 80%, to the nucleotide sequence shown in SEQ ID NO.1. Furthermore it is preferred that the DNA molecule has a length of at least 15 preferably of at least 20 nucleotides.

The DNA sequence of the adhesin gene alpB shown in SEQ ID NO.1 codes for a polypeptide of 518 amino acids. The amino acid sequence of this polypeptide denoted AlpB is shown in SEQ ID NO. 1 and 2. An analysis of the N-terminal region of the amino acid sequence of AlpB suggests that the polypeptide has a classical prokaryotic signal sequence. A comparison at the amino acid level between AlpB and the polypeptide AlpA described in the German Patent Application 195 21 312.2 whose amino acid sequence is shown in SEQ ID NO.3 and 4 shows that 46% of the entire amino acid sequence is identical in both polypeptides. The C-terminal part (amino acids 341–518) even exhibits 66% identity.

Defect mutants in the alpB gene which were produced by inserting the transposon TnMax9 at two different positions on the alpB gene do not bind to tissue sections of gastric epithelial cells. Since a stable expression of AlpA was detected in these alpB mutants, the defect in the alpB gene must be directly responsible for the loss of adherence of the alpB mutant.

There is a functional connection between AlpA and AlpB in that AlpB and AlpA can presumably together form a complex. This complex could be present as a heterodimeric or/and multimeric aggregate which is effective as a functional adhesin. The loss of one subunit whether AlpA or AlpB can already lead to loss of the function of the adhesin complex and thus to adherence defects of the bacteria.

Therefore a further subject matter of the present invention is a DNA molecule which comprises sequence regions of the alpB gene and of the alpA gene that are fused together. In particular this is a DNA molecule in which the sequence defined above under (a), (b) and (c) is fused with (d) the nucleotide sequence shown in SEQ ID NO.3

(e) a nucleotide sequence which corresponds to the sequence according to (d) within the scope of the degeneracy of the genetic code or (f) a nucleotide sequence which hybridizes with the sequences according to (d) or/and (e) under stringent conditions.

A preferred example of such a fused DNA molecule contains one or several sections from each of the adhesin genes alpB (SEQ ID NO.1) and alpA (SEQ ID NO.3). The lengths of these sections is preferably at least 18 nucleotides, particularly preferably at least 30 nucleotides and most preferably at least 60 nucleotides.

A further subject matter of the present invention is a vector which contains at least one copy of a DNA molecule according to the invention. This vector can be any prokaryotic or eukaryotic vector on which the DNA sequence according to the invention is located preferably under the control of an expression signal (promoter, operator, enhancer etc.). Examples of prokaryotic vectors are chromosomal vectors such as for example bacteriophages (e.g. bacteriophage λ) and extrachromosomal vectors such as plasmids, whereby circular plasmid vectors are especially preferred. Suitable prokaryotic vectors are e.g. described by Sambrook et al., Supra, chapters 1 to 4.

On the other hand the vector according to the invention can also be a eukaryotic vector e.g. a yeast vector or a vector suitable for higher cells (e.g. a plasmid vector, viral vector, plant vector). Such vectors are for example described by Sambrook et al., Supra, chapter 16.

Yet a further subject matter of the present invention is a cell which is transformed with a vector according to the invention. In a preferred embodiment the cell is a prokaryotic cell preferably a gram-negative prokaryotic cell particularly preferably an *E. coli* cell. However, on the other hand the cell according to the invention can also be a eukaryotic cell such as a fungal cell (e.g. yeast), an animal or a plant cell.

The invention also concerns a polypeptide which is coded by a DNA molecule according to the invention. The polypeptide is preferably capable of adhering to human cells and comprises (a) the amino acid sequence shown in SEQ ID NO.2 or (b) an amino acid sequence that immunologically cross-reacts with the sequence according to (a).

The polypeptide according to the invention preferably has a homology of at least 80% and most preferably of at least 90% to the amino acid sequence shown in SEQ ID NO.2.

The polypeptides according to the invention are preferably produced by transforming a cell with a DNA molecule or vector according to the invention, culturing the transformed cell under conditions in which expression of the polypeptide takes place and isolating the polypeptide from the cell or/and the culture supernatant. In this process the polypeptide according to the invention can be obtained as a fusion polypeptide as well as a non-fusion polypeptide.

Yet a further subject matter of the present invention are fusion polypeptides which each contain one or several sections from the polypeptides AlpB (SEQ ID NO.2) and AlpA (SEQ ID NO.4). The lengths of these sections is at least 6, preferably at least 10 and most preferably at least 20 amino acids.

Since the AlpB protein can form a functionally active complex with the AlpA protein disclosed in DE 195 21 312.2, the present invention also concerns a polypeptide complex which contains at least two polypeptide components the first component being coded by the alpB sequence or a sequence derived therefrom and the second component being coded by the alpA sequence or a sequence derived therefrom in particular by a DNA molecule which comprise
(d) the nucleotide sequence shown in SEQ ID NO.3
(e) a nucleotide sequence which corresponds to the sequence according to (d) within the scope of the degeneracy of the genetic code or
(f) a nucleotide sequence which hybridizes with the sequences according to (d) or/and (e) under stringent conditions.

The second polypeptide i.e. the AlpA component of the complex preferably comprises the amino acid sequence shown in SEQ ID NO.4, an amino acid sequence which is at least 80% and preferably at least 90% homologous to this sequence or an amino acid sequence which immunologically cross-reacts with these sequences.

The polypeptide AlpB according to the invention or parts thereof can be used as an immunogen to produce antibodies. The present invention therefore also concerns an antibody which is directed against a polypeptide according to the invention or a complex according to the invention. The antibody is preferably directed against the N-terminus e.g. the first 340 and in particular the first 250 amino acids of the amino acid sequence shown in SEQ ID NO.2.

Yet a further aspect of the present invention concerns a pharmaceutical composition which contains a DNA molecule according to the invention, a polypeptide according to the invention, a polypeptide complex according to the invention or an antibody according to the invention as the active substance optionally together with common pharmaceutical auxiliary substances, diluents, additives and carriers.

The pharmaceutical composition according to the invention can be used on the one hand to diagnose a *Helicobacter pylori* infection. The diagnosis at the nucleic acid level is preferably carried out by using hybridization probes which contain a DNA sequence according to the invention that is specific for the alpB gene or by amplification using DNA molecules according to the invention as primers. At the protein level the diagnostics are preferably carried out with the aid of the antibodies according to the invention.

On the other hand the pharmaceutical composition can also be used to prevent or fight a *Helicobacter pylori* infection. For therapeutic applications the AlpB polypeptide or parts thereof optionally together with the AlpA polypeptide or parts thereof are used to produce an active vaccine or the antibody is used to produce a passive vaccine.

It is intended to further elucidate the invention by the following examples and figures.

FIG. 1 shows a restriction map of the plasmid pMu140 which contains the regulatory region and the 5' end of the alpA gene (SEQ ID NO.3). The alpA gene is inactivated by insertion of the transposon TnMax9 (see triangle labelled TnMax9). When the plasmid is expressed an alpA-β-lactamase fusion protein is obtained. pMu140 is the original clone from the mutant gene bank from which the adherence-defective *H. pylori* strain P1-140 was obtained by retransformation and homologous recombination.

Figure 2:
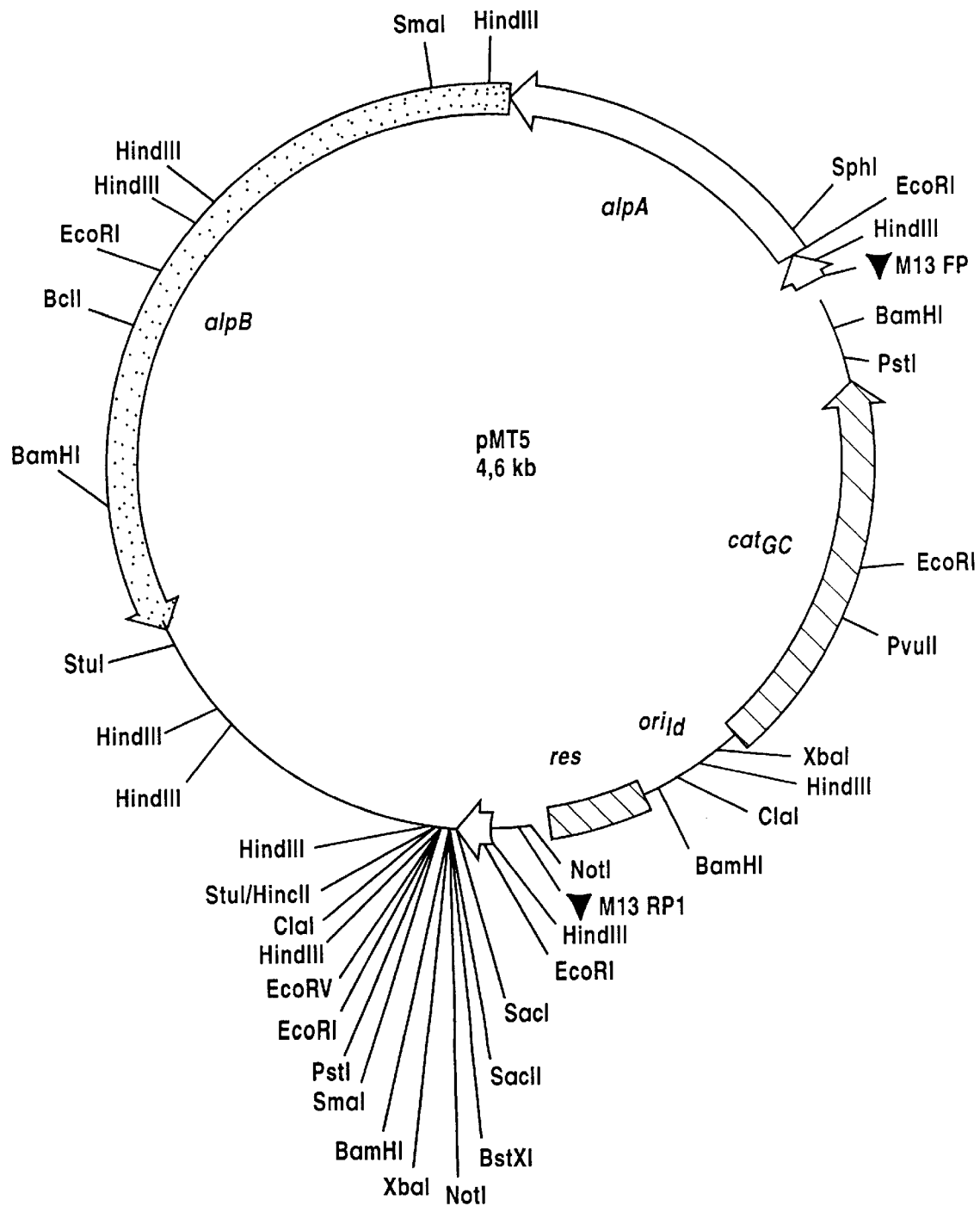

FIG. 2 shows a restriction map of the plasmid pMT5 which contains a part of the alpA gene and the entire alpB gene (SEQ ID NO.1). The origin of replication $ori_{fd}$ and the chloramphenicol transferase gene $cat_{GC}$ from the transposon TnMax 9 were used for the selective cloning back of the mutated alpA gene locus and of the flanking alpB gene region. Res denotes the resolution site of TnMax9 and IR denotes the inverted repeats of the transposon. M13-FP and M12-RP1 denote regions which contain the sequences of M12-FORWARD and REVERSE sequencing primers. The polylinker region between the cloning sites SacI and StuI originates from the plasmid pBluescript II KS.

FIG. 3A and 3B shows an amino acid sequence comparison of the adhesins AlpA and AlpB. (A) The sequence comparison was carried out using the GCG program BEST-FIT (Devereux et al., 1984) and covers the entire polypeptides AlpA and AlpB. Vertical lines denote identical amino acids; points show conserved amino acid substitutions. The degree of similarity or identity between both sequences is stated at the end of the sequence. (B) A significantly higher degree of identity can be seen in the C-terminal region of both poly-peptides (position 341–518) which is presumably responsible for the integration of the proteins into the external bacterial membrane. The C-terminal region of five amino acids which ends with a phenylalanine (F) is also typical which in the case of a secreted protein of a gram-negative bacterium indicates an insertion into the external membrane (Struyvé et al., 1991).

SEQ ID NO.1 shows the nucleotide sequence of the *H. pylori* adherence gene alpB and the corresponding amino acid sequence.

SEQ ID NO.2 shows the amino acid sequence of the AlpB adherence polypeptide from *H. pylori*.

SEQ ID NO.3 shows the nucleotide sequence of the *H. pylori* adherence gene alpA and the corresponding amino acid sequence.

SEQ ID NO.4 shows the amino acid sequence of the AlpA adherence polypeptide from *H. pylori*.

EXAMPLE 1
Construction of a *H. pylori* plasmid gene bank

A plasmid gene bank of the chromosomal DNA of the *H. pylori* wild-type strain 69A was set up. For this the chromosomal DNA was isolated from *H. pylori* by the method of Leying et al. (1992) and partially cleaved with each of the restriction endonucleases Sau3AI and HpaII. Subsequently the DNA fragments were separated on a preparative agarose gel and fragments of 3–6 kb were eluted from the gel. These DNA fragments were ligated into the plasmid vector pMin2 which was specially constructed for this purpose and had been cleaved with the restriction enzymes BglII and ClaI, ligated (T4 ligase) and the ligation mixture was transformed into the *E. coli* strain E 181 which is a derivative of the strain HB101 (Bayer and Roulland-Dussoix, 1969) containing the lysogenes λphages λCH616 and had already been transformed with the transposon TnMax9. In this process ca. 2400 independent transformants were obtained.

The *E. coli* strain DH5a containing the minimal vector pMin2 is deposited at the "Deutsche Sammlung von Mikroorganismen und Zellkulturen GmbH (DSM)", Mascheroder Weg 1b, D-38124 Braunschweig under the file number 10007. The *E. coli* strain E 181 containing the transposon derivative pTnMax9 is deposited at the DSM under the file number 10008.

EXAMPLE 2
Isolation of *H. pylori* mutants

In order to carry out the transposon mutagenesis 10 transformants were pooled in each case and mutually induced by which means a total of 190 pools each with 10–20 clones were treated further. 191 ampicillin resistant *E. coli* plasmid clones were isolated from this mutagenesis which carried independently mutated H. pylori genes. These 192 plasmids were isolated from *E. coli* and used for the retransformation of the *H. pylori* strain 69A. 135 *H. pylori* mutants were isolated from these 192 transformations which were presumably mutated in genes which code for secretory proteins. The *H. pylori* mutant collection was then tested in a screening assay for *H. pylori* mutants which had lost their ability to bind to KatoIII epithelial cells.

For this the mutants were labelled with FITC and cultured for 1 hour at 37° C. together with the epithelial cells. The test for adherence was carried out directly by observation with a fluorescence microscope. 2 mutants were found in this case (No. P1-140 and P1-179a) which showed a greatly reduced adherence.

Both mutants also exhibited no adherence in the second adherence model, the tissue sections of human stomach. The *H. pylori* wild-type strain as well as all further mutants also showed a strong adherence in this model.

The plasmid pMu140 used to produce the mutant strain P1-140 is shown in FIG. 1. The plasmid pMu179a (not shown) was used to produce the mutant strain P1-179a. Independent transformations of both plasmids in H. pylori 69A led to the identified adherence defect which proved that no secondary mutations had occurred in the bacterial chromosome but rather that the TnMax9 insertion in the cloned adhesin gene led to the observed phenotype of the *H. pylori* mutants. The mapping and sequencing of the genes of the plasmid clones pMu140 and pMu179 inactivated by the transposon TnMax9 showed that both clones were the same gene; the transposon was only inserted at different sites. Since the coded protein is a lipoprotein i.e. a protein which is anchored in the membrane with a lipid anchor, the corresponding gene was denoted AlpA (adherence-associated lipoprotein A). Our data from computer secondary structure predictions of membrane proteins and of certain conserved protein sequences at the C-terminus of the protein (C-terminal phenylalanine; Struyvé et al., 1991) argue in favour of an integral membrane protein incorporated into the outer membrane of the gram-negative bacteria.

EXAMPLE 3

Identification of the alpB adherence gene

During the genetic characterization of the AlpB gene locus the flanking genomic sequences were cloned in *E. coli* and sequenced. The cloning of the downstream alpA-flanking region was achieved by back-cloning the TnMax9-insertion from the chromosome of *H. pylori*. Chromosomal DNA of the mutant P1-179a (see example 2) was cleaved with the restriction endonucleases SacI and StuI, the DNA fragments that were formed were circularised together with a SacI-HincII fragment from the polylinker of the plasmid pBluescript II KS using T4 ligase and transformed into competent *E. coli* E131 cells which were selected on chloramphenicol.

All transformants obtained should contain the mutated alpA gene and have flanking sequences since the replication and propagation could only take place via the origin of replication $ori_{fd}$ inserted chromosomally by TnMax9 and via the chloramphenicol resistance gene located on TnMax9. One of the recombinant plasmids (FIG. 2) obtained pMT5 was analysed further.

Sequencing of pMT5 and subclones constructed therefrom show that there was the start of a further open reading frame following the alpA gene (67 nucleotides after the stop codon) which code for a polypeptide of 518 amino acids and was denoted alpB (SEQ ID NO.1 and 2). Based on the genetic organisation one can assume an operon and alpA and alpB are presumably transcribed by a single promoter (polycystronic mRNA).

The AlpB gene product has exactly the same number of amino acids as AlpA. An analysis of the N-terminal region of the AlpB polypeptide sequence indicates the presence of a classic prokaryotic signal sequence which indicates a secretory polypeptide. A comparison at the amino acid level between AlpA and AlpB shows a 46% identity over the entire polypeptide. The C-terminal part (amino acids 341–518) shows a 66% identity (FIG. 3).

EXAMPLE 4

Functional connection between the adherence genes AlpA and AlpB

In order to investigate a functional connection between AlpA and AlpB, two TnMax9 transposon insertions were introduced at various positions in the alpB gene (pos. 97 and pos. 1108) and transferred by natural transformation into the genome of *H. pylori* 69a. The correct insertion of the transposon into the *H. pylori* chromosome and thus the inactivation of the alpB gene was verified by Southern Blot hybridization.

The resulting alpB defect mutants were analysed for their ability to bind to gastric epithelial cells. It was found that both alpB mutants did not bind to gastric epithelial cells from tissue sections.

The stable expression of AlpA in the alpB mutant could be proven by an immunoblot. This shows that AlpB is directly responsible for the adherence defect of the alpB mutant. As a result of the structure prediction and the high homology in the C-terminal region of both polypeptides one can assume that AlpB is also present inserted into the external bacterial membrane and may be able to form a complex with AlpA. This complex can be effective as a functional adhesin as a heterodimeric or multimeric aggregate whereas the loss of a subunit, whether AlpA or AlpB, already leads to a loss of function of the adhesin complex and thus may lead to an adherence defect of the bacteria.

LITERATURE

Alper, J. (1993) Ulcers as an infectious disease. Science 260: 159–160.

Bizzozero, G. (1893) Ueber die schlauchförmigen Drusen des Magendarmkanals und die Beziehungen ihres Epithels zu dem Oberflächenepithel der Schleimhaut. Arch Mikr Anast 42: 82.

Blaser, M. J. (1992) Hypotheses on the pathogenesis and natural history of *Helicobacter pylori* induced inflammation. Gastroenterol 102: 720–727.

Borén, T., Falk, P., Roth, K. A., Larson, G., Normark, S. (1993) Attachment of *Helicobacter pylori* to gastric epithelium mediated by blood group antigens. Science 262: 1892–1895.

Boyer, H. W. and Roulland-Dussoix, D. (1969) A complementation analysis of the restriction and modification of DNA in *Escherichia coli*. J. Mol. Biol. 41: 459–472.

Devereux, J., Haeberli, P. and Smithies, O. (1984) A comprehensive set of sequence analysis programs for the vax. Nucl. Acids Res 12: 387–395.

Evans, D. G., Karjalainen, T. K., Evans, D. J., Jr., Graham, D. Y., Lee, C. -H. (1993) Cloning, nucleotide sequence, and expression of a gene encoding an adhesin subunit protein of *Helicobacter pylori*. J. Bacteriol 175: 674–683.

Falk, P., Roth, K. A., Boren, T., Westblom, T. U., Gordon, J. I., Normark, S. (1993) An in vitro adherence assay reveals that *Helicobacter pylori* exhibits cell lineage-specific tropism in the human gastric epithelium. Proc. Natl. Acad. Sci USA 90: 2035–2039.

Goodwin, C. S., Armstrong, J. A., Chilvers, T., Peters, M., Collins, M. D., Sly, L., McConnell, W., Harper, W. E. S. (1989) Transfer of *Campylobacter pylori* and Campylobacter mustelae to Helicobacter gen. nov. as *Helicobacter pylori* comb. nov. and *Helicobacter mustelae* comb. nov., respectively. Int. J. Syst. Bact 39: 397–405.

Isaacson, P. G., Spencer, J. (1993) Is gastric lymphoma an infectious disease? Hum. Pathol. 24: 569–570.

Lee, A., Fox, J., Hazell, S. (1993) Pathogenicity of *Helicobacter pylori*: a perspective. Infect. Immun. 61: 1601–1610.

Leying, H., Suerbaum, S., Geis, G., Haas, R. (1992) Characterisation of flaA, a *Helicobacter pylori* flagellin gene. Mol. Microbiol 6: 2863–2874.

Mai, U. E. H., Perez-Perez, I., Wahl, L. M., Wahl, S. M., Blaser, M. J., Smith, P. D. (1991) Soluble surface proteins from *Helicobacter pylori* activate monocytes/macrophages by lipopolysaccharide-independent mechanism. J. Clin Invest. 87: 894–900.

Malfertheiner P. (1994) *Helicobacter pylori*—Von der Grundlage zur Therapie. Bayerdörfer E., Birkholz S., B örsch G. et al., (eds.) Stuttgart, New York: Georg Thieme Verlag; p. 1–104.

Marshall, B. J., Royce, J., Annear, D. I., Goodwin, C. S., Pearman, J. W., Warren, J. R., Armstrong, J. A. (1984) original isolation of *Campylobacter pyloridis* from human gastric mucosa. Microbios. Lett. 25: 83–88.

Michetti, P., Corthesy-Theulaz, I., Davin, C., Haas, R., Vaney, A. C., Heitz, M., Bille, J., Kraehenbuhl, J. P., Saraga, E., Blum, A. L. (1994) Immunization of Balb/c mice against *Helicobacter felis* infection with *Helicobacter pylori* urease. Gastroenterol 107: 1002–1011.

Nomura, A., Stemmermann, G. N., Chyou, P. H., Kato, I., Perez—Perez, G. I., Blaser, M. J. (1991) *Helicobacter pylori* infection and gastric carcinoma among japanese americans in Hawaii. N Engl. J. Med. 325: 1132–1136.

Parkin, D. M., Läärä, E., Muir, C. S. (1988) Estimates of the worldwide frequency of sixteen major cancers in 1980. Int. J. Cancer 41: 184–197.

Parsonnet, J., Friedmann, G. D., Vandersteen, D. P., Chang, Y., Vogelman, J. H., Orentreich, N., Sibley, R. K. (1991) *Helicobacter pylori* infection and the risk of gastric carcinoma. N. Engl. J. Med. 325: 1227–1231.

Schöffl, F., Puhler, A., Altenbuchner, J. and Schmitt, R. (1981) The tetracycline resistance transposons Tn1721 and Tn1771 have three 38-base-pair repeats and generate five-base-pair repeats. Mol. Gen. Genet 181: 87–94.

Sipponen, P. (1992) Natural history of gastritis and its relationship to peptic ulcer disease. Digestion 51: 70–75.

Sipponen, P., Hyvärinen, H. (1993) Role of *Helicobacter pylori* in the pathogenesis of gastritis, peptic ulcer and gastric cancer. Scand. J. Gastroenterol 28: 3–6.

Solnick, J. V., Tompkins, L. S. (1993) *Helicobacter pylori* and gastroduodenal disease: pathogenesis and host-parasite interaction. Infect Ag Dis 1: 294–309.

Stolte, M., Eidt, S. (1993) Healing gastric MALT lymphomas by eradicating *H. pylori*. Lancet 342: 568.

Struyvé, M., Moons, M., Tommassen, J. (1991) Carboxy-terminal phenylalanine is essential for the correct assembly of a bacterial outer membrane protein. J. Mol. Biol. 218: 141–148.

Taylor, D. N., Blaser, M. J. (1991) The epidemiology of *Helicobacter pylori* infection. Epidemiol Rev. 13: 42–59.

Warren, J. R., Marshall, B. (1983) Unidentified curved bacilli on gastric epithelium in active chronic gastritis. Lancet i: 1273–1275.

We claim:

1. An isolated and purified DNA molecule, comprising a nucleotide sequence selected from the group consisting of:
   (a) the nucleotide sequence shown in SEQ ID NO:1;
   (b) a nucleotide sequence which encodes the amino acid sequence according to SEQ ID NO:2; and
   (c) a nucleotide sequence which hybridizes with the sequences according to (a) or (b) under stringent conditions, wherein said stringent conditions are washing for 1 hour with 1× SSC and 0.1% SDS at 55° C.
   wherein said nucleotide sequence codes for a polypeptide with the ability to adhere bacteria to human cells.

2. A DNA molecule as claimed in claim 1, wherein at the nucleotide level it has a homology of at least 80% to the nucleotide sequence shown in SEQ ID NO:1.

3. DNA molecule as claimed in claim 1, wherein it codes for a section of the polypeptide and has a length of at least 15 nucleotides provided that the DNA molecule is not the nucleotide sequence EMBL AC U22062 pos 8813–8827 (GCAGTGGTGGTGGTG) (SEQ. ID NO.5).

4. DNA molecule as claimed in claim 1, which is fused with
   (d) the nucleotide sequence shown in SEQ ID NO.3;
   (e) a nucleotide sequence which encodes the same amino acid sequence as SEQ ID NO:4; or
   (f) a nucleotide sequence which hybridizes with the sequences according to (d) or (e) under stringent conditions wherein said stringent conditions are washing for 1 hour with 1× SSC and 0.1% SDS at 55° C.

5. A vector, wherein it contains at least one copy of a DNA molecule as claimed in claim 1.

6. An isolated cell, wherein it is transformed with a vector as claimed in claim 5.

7. Process for the production of a polypeptide,
   wherein a cell is transformed with a DNA molecule as claimed in claim 1, the transformed cell is cultured under conditions in which an expression of the polypeptide takes place and the polypeptide is isolated from the cell or the culture supernatant, or from the cell and the culture supernatant.

8. A diagnostic reagent comprising the DNA molecule of claim 1, and at least one member selected from the group consisting of a diluent, additive, and carrier.

9. A method of diagnosing a *Helicobacter pylori* infection comprising
   obtaining a biological sample from a patient suspected of having a *Helicobacter pylori* infection,
   reacting said biological sample with the diagnostic reagent of claim 8 under conditions suitable for hybridization or amplification, and
   detecting any hybridization or amplification as an indication of the presence of a *Helicobacter pylori* infection.

* * * * *

SEQUENCE LISTING

```
<160> NUMBER OF SEQ ID NOS: 5

<210> SEQ ID NO 1
<211> LENGTH: 1557
<212> TYPE: DNA
<213> ORGANISM: Helicobacter pylori
<220> FEATURE:
<221> NAME/KEY: CDS
<222> LOCATION: (1)..(1554)

<400> SEQUENCE: 1 atg aca caa tct caa aaa gta aga ttc tta gcc cct tta agc cta gcg      48
Met Thr Gln Ser Gln Lys Val Arg Phe Leu Ala Pro Leu Ser Leu Ala
 1               5                  10                  15 tta agc ttg agc ttc aat cca gtg ggc gct gaa gaa gat ggg ggc ttt      96
Leu Ser Leu Ser Phe Asn Pro Val Gly Ala Glu Glu Asp Gly Gly Phe
             20                  25                  30 atg acc ttt ggg tat gaa tta ggt cag gtg gtc caa caa gtg aaa aac     144
Met Thr Phe Gly Tyr Glu Leu Gly Gln Val Val Gln Gln Val Lys Asn
         35                  40                  45 ccg ggt aaa atc aaa gcc gaa gaa tta gcc ggc ttg tta aac tct acc     192
Pro Gly Lys Ile Lys Ala Glu Glu Leu Ala Gly Leu Leu Asn Ser Thr
     50                  55                  60 aca aca aac aac acc aat atc aat att gca ggc aca gga ggc aat gtc     240
Thr Thr Asn Asn Thr Asn Ile Asn Ile Ala Gly Thr Gly Gly Asn Val
 65                  70                  75                  80
```

-continued

| | |
|---|---|
| gcc ggg act ttg ggc aac ctt ttt atg aac caa tta ggc aat ttg att<br>Ala Gly Thr Leu Gly Asn Leu Phe Met Asn Gln Leu Gly Asn Leu Ile<br>                85                            90                      95 | 288 |
| gat ttg tat ccc act ttg aac act agt aat atc aca caa tgt ggc act<br>Asp Leu Tyr Pro Thr Leu Asn Thr Ser Asn Ile Thr Gln Cys Gly Thr<br>               100                        105                     110 | 336 |
| act aat agt ggt agt agt agt agt ggt ggt ggt gcg gcc aca gcc gct<br>Thr Asn Ser Gly Ser Ser Ser Ser Gly Gly Gly Ala Ala Thr Ala Ala<br>            115                      120                   125 | 384 |
| gct act act agc aat aag cct tgt ttc caa ggt aac ctg gat ctt tat<br>Ala Thr Thr Ser Asn Lys Pro Cys Phe Gln Gly Asn Leu Asp Leu Tyr<br>130                      135                     140 | 432 |
| aga aaa atg gtt gac tct atc aaa act ttg agt caa aac atc agc aag<br>Arg Lys Met Val Asp Ser Ile Lys Thr Leu Ser Gln Asn Ile Ser Lys<br>145                      150                     155                 160 | 480 |
| aat atc ttt caa ggc aac aac aac acc acg agc caa aat ctc tcc aac<br>Asn Ile Phe Gln Gly Asn Asn Asn Thr Thr Ser Gln Asn Leu Ser Asn<br>               165                       170                   175 | 528 |
| cag ctc agt gag ctt aac acc gct agc gtt tat ttg act tac atg aac<br>Gln Leu Ser Glu Leu Asn Thr Ala Ser Val Tyr Leu Thr Tyr Met Asn<br>            180                      185                   190 | 576 |
| tcg ttc tta aac gcc aat aac caa gcg ggt ggg att ttt caa aac aac<br>Ser Phe Leu Asn Ala Asn Asn Gln Ala Gly Gly Ile Phe Gln Asn Asn<br>               195                       200                   205 | 624 |
| act aat caa gct tat gga aat ggg gtt acc gct caa caa atc gct tat<br>Thr Asn Gln Ala Tyr Gly Asn Gly Val Thr Ala Gln Gln Ile Ala Tyr<br>       210                     215                     220 | 672 |
| atc cta aag caa gct tca atc act atg ggg cca agc ggt gat agc ggt<br>Ile Leu Lys Gln Ala Ser Ile Thr Met Gly Pro Ser Gly Asp Ser Gly<br>225                      230                     235                 240 | 720 |
| gct gcc gca gcg ttt ttg gat gcc gct tta gcg caa cat gtt ttc aac<br>Ala Ala Ala Ala Phe Leu Asp Ala Ala Leu Ala Gln His Val Phe Asn<br>               245                       250                   255 | 768 |
| tcc gct aac gcc ggg aac gat ttg agc gct aag gaa ttc act agc ttg<br>Ser Ala Asn Ala Gly Asn Asp Leu Ser Ala Lys Glu Phe Thr Ser Leu<br>            260                      265                   270 | 816 |
| gtg caa aat atc gtc aat aat tct caa aac gct tta acg cta gcc aac<br>Val Gln Asn Ile Val Asn Asn Ser Gln Asn Ala Leu Thr Leu Ala Asn<br>               275                       280                   285 | 864 |
| aac gct aac atc agc aat tca aca ggc tat caa gtg agc tat ggc ggg<br>Asn Ala Asn Ile Ser Asn Ser Thr Gly Tyr Gln Val Ser Tyr Gly Gly<br>            290                      295                   300 | 912 |
| aat att gat caa gcg cga tct acc caa cta tta aac aac acc aca aac<br>Asn Ile Asp Gln Ala Arg Ser Thr Gln Leu Leu Asn Asn Thr Thr Asn<br>305                      310                     315                 320 | 960 |
| act ttg gct aaa gtt agc gct ttg aat aac gag ctt aaa gct aac cca<br>Thr Leu Ala Lys Val Ser Ala Leu Asn Asn Glu Leu Lys Ala Asn Pro<br>               325                       330                   335 | 1008 |
| tgg ctt ggg aat ttt gcc gcc ggt aac agc tct caa gtg aat gcg ttt<br>Trp Leu Gly Asn Phe Ala Ala Gly Asn Ser Ser Gln Val Asn Ala Phe<br>            340                      345                   350 | 1056 |
| aac ggg ttt atc act aaa atc ggt tac aag caa ttc ttt ggg gaa aac<br>Asn Gly Phe Ile Thr Lys Ile Gly Tyr Lys Gln Phe Phe Gly Glu Asn<br>               355                       360                   365 | 1104 |
| aag aat gtg ggc tta cgc tac tac ggc ttc ttc agc tat aac ggc gcg<br>Lys Asn Val Gly Leu Arg Tyr Tyr Gly Phe Phe Ser Tyr Asn Gly Ala<br>       370                     375                     380 | 1152 |
| ggc gtg ggt aat ggc cct act tac aat caa gtc aat ttg ctc act tat<br>Gly Val Gly Asn Gly Pro Thr Tyr Asn Gln Val Asn Leu Leu Thr Tyr<br>385                      390                     395                 400 | 1200 |

-continued

```
ggg gtg ggg act gat gtg ctt tac aat gtg ttt agc cgc tct ttt ggt    1248
Gly Val Gly Thr Asp Val Leu Tyr Asn Val Phe Ser Arg Ser Phe Gly
                405                 410                 415 agt agg agt ctt aat gcg ggc ttc ttt ggg ggg atc caa ctc gca ggg    1296
Ser Arg Ser Leu Asn Ala Gly Phe Phe Gly Gly Ile Gln Leu Ala Gly
            420                 425                 430 gat act tac atc agc acg cta aga aac agc tct cag ctt gcg agc aga    1344
Asp Thr Tyr Ile Ser Thr Leu Arg Asn Ser Ser Gln Leu Ala Ser Arg
        435                 440                 445 cct aca gcg acg aaa ttc caa ttc ttg ttt gat gtg ggc tta cgc atg    1392
Pro Thr Ala Thr Lys Phe Gln Phe Leu Phe Asp Val Gly Leu Arg Met
    450                 455                 460 aac ttt ggt atc ttg aaa aaa gac ttg aaa agc cat aac cag cat tct    1440
Asn Phe Gly Ile Leu Lys Lys Asp Leu Lys Ser His Asn Gln His Ser
465                 470                 475                 480 ata gaa atc ggt gtg caa atc cct acg att tac aac act tac tat aaa    1488
Ile Glu Ile Gly Val Gln Ile Pro Thr Ile Tyr Asn Thr Tyr Tyr Lys
                485                 490                 495 gct ggc ggt gct gaa gtg aaa tac ttc cgc cct tat agc gtg tat tgg    1536
Ala Gly Gly Ala Glu Val Lys Tyr Phe Arg Pro Tyr Ser Val Tyr Trp
            500                 505                 510 gtc tat ggc tac gcc ttc taa                                        1557
Val Tyr Gly Tyr Ala Phe
        515

<210> SEQ ID NO 2
<211> LENGTH: 518
<212> TYPE: PRT
<213> ORGANISM: Helicobacter pylori

<400> SEQUENCE: 2

Met Thr Gln Ser Gln Lys Val Arg Phe Leu Ala Pro Leu Ser Leu Ala
1               5                   10                  15

Leu Ser Leu Ser Phe Asn Pro Val Gly Ala Glu Glu Asp Gly Gly Phe
            20                  25                  30

Met Thr Phe Gly Tyr Glu Leu Gly Gln Val Val Gln Val Lys Asn
        35                  40                  45

Pro Gly Lys Ile Lys Ala Glu Glu Leu Ala Gly Leu Leu Asn Ser Thr
    50                  55                  60

Thr Thr Asn Asn Thr Asn Ile Asn Ile Ala Gly Thr Gly Gly Asn Val
65                  70                  75                  80

Ala Gly Thr Leu Gly Asn Leu Phe Met Asn Gln Leu Gly Asn Leu Ile
            85                  90                  95

Asp Leu Tyr Pro Thr Leu Asn Thr Ser Asn Ile Thr Gln Cys Gly Thr
        100                 105                 110

Thr Asn Ser Gly Ser Ser Ser Gly Gly Ala Ala Thr Ala Ala
    115                 120                 125

Ala Thr Thr Ser Asn Lys Pro Cys Phe Gln Gly Asn Leu Asp Leu Tyr
    130                 135                 140

Arg Lys Met Val Asp Ser Ile Lys Thr Leu Gln Asn Ile Ser Lys
145                 150                 155                 160

Asn Ile Phe Gln Gly Asn Asn Asn Thr Thr Ser Gln Asn Leu Ser Asn
                165                 170                 175

Gln Leu Ser Glu Leu Asn Thr Ala Ser Val Tyr Leu Thr Tyr Met Asn
            180                 185                 190

Ser Phe Leu Asn Ala Asn Asn Gln Ala Gly Gly Ile Phe Gln Asn Asn
        195                 200                 205
```

-continued

```
Thr Asn Gln Ala Tyr Gly Asn Gly Val Thr Ala Gln Gln Ile Ala Tyr
    210                 215                 220

Ile Leu Lys Gln Ala Ser Ile Thr Met Gly Pro Ser Gly Asp Ser Gly
225                 230                 235                 240

Ala Ala Ala Ala Phe Leu Asp Ala Ala Leu Ala Gln His Val Phe Asn
                245                 250                 255

Ser Ala Asn Ala Gly Asn Asp Leu Ser Ala Lys Glu Phe Thr Ser Leu
            260                 265                 270

Val Gln Asn Ile Val Asn Ser Gln Asn Ala Leu Thr Leu Ala Asn
        275                 280                 285

Asn Ala Asn Ile Ser Asn Ser Thr Gly Tyr Gln Val Ser Tyr Gly Gly
    290                 295                 300

Asn Ile Asp Gln Ala Arg Ser Thr Gln Leu Leu Asn Asn Thr Thr Asn
305                 310                 315                 320

Thr Leu Ala Lys Val Ser Ala Leu Asn Asn Glu Leu Lys Ala Asn Pro
                325                 330                 335

Trp Leu Gly Asn Phe Ala Ala Gly Asn Ser Ser Gln Val Asn Ala Phe
            340                 345                 350

Asn Gly Phe Ile Thr Lys Ile Gly Tyr Lys Gln Phe Phe Gly Glu Asn
        355                 360                 365

Lys Asn Val Gly Leu Arg Tyr Tyr Gly Phe Phe Ser Tyr Asn Gly Ala
    370                 375                 380

Gly Val Gly Asn Gly Pro Thr Tyr Asn Gln Val Asn Leu Leu Thr Tyr
385                 390                 395                 400

Gly Val Gly Thr Asp Val Leu Tyr Asn Val Phe Ser Arg Ser Phe Gly
                405                 410                 415

Ser Arg Ser Leu Asn Ala Gly Phe Phe Gly Gly Ile Gln Leu Ala Gly
            420                 425                 430

Asp Thr Tyr Ile Ser Thr Leu Arg Asn Ser Ser Gln Leu Ala Ser Arg
        435                 440                 445

Pro Thr Ala Thr Lys Phe Gln Phe Leu Phe Asp Val Gly Leu Arg Met
    450                 455                 460

Asn Phe Gly Ile Leu Lys Lys Asp Leu Lys Ser His Asn Gln His Ser
465                 470                 475                 480

Ile Glu Ile Gly Val Gln Ile Pro Thr Ile Tyr Asn Thr Tyr Lys
                485                 490                 495

Ala Gly Gly Ala Glu Val Lys Tyr Phe Arg Pro Tyr Ser Val Tyr Trp
            500                 505                 510

Val Tyr Gly Tyr Ala Phe
        515
```

<210> SEQ ID NO 3
<211> LENGTH: 1557
<212> TYPE: DNA
<213> ORGANISM: Helicobacter pylori
<220> FEATURE:
<221> NAME/KEY: CDS
<222> LOCATION: (1)..(1554)

<400> SEQUENCE: 3

```
atg ata aaa aag aat aga acg ctg ttt ctt agt cta gcc ctt tgc gct    48
Met Ile Lys Lys Asn Arg Thr Leu Phe Leu Ser Leu Ala Leu Cys Ala
  1               5                  10                  15 agc ata agt tat gcc gaa gat gat gga ggg ttt ttc acc gtc ggt tat    96
Ser Ile Ser Tyr Ala Glu Asp Asp Gly Gly Phe Phe Thr Val Gly Tyr
             20                  25                  30
```

-continued

| | | |
|---|---|---|
| cag ctc ggg caa gtc atg caa gat gtc caa aac cca ggc ggc gct aaa<br>Gln Leu Gly Gln Val Met Gln Asp Val Gln Asn Pro Gly Gly Ala Lys<br>35                               40                         45 | 144 |
| agc gac gaa ctc gcc aga gag ctt aac gct gat gta acg aac aac att<br>Ser Asp Glu Leu Ala Arg Glu Leu Asn Ala Asp Val Thr Asn Asn Ile<br>50                           55                        60 | 192 |
| tta aac aac aac acc gga ggc aac atc gca ggg gcg ttg agt aac gct<br>Leu Asn Asn Asn Thr Gly Gly Asn Ile Ala Gly Ala Leu Ser Asn Ala<br>65                      70                       75                  80 | 240 |
| ttc tcc caa tac ctt tat tcg ctt tta ggg gct tac ccc aca aaa ctc<br>Phe Ser Gln Tyr Leu Tyr Ser Leu Leu Gly Ala Tyr Pro Thr Lys Leu<br>            85                       90                       95 | 288 |
| aat ggt agc gat gtg tct gcg aac gct ctt tta agt ggt gcg gta ggc<br>Asn Gly Ser Asp Val Ser Ala Asn Ala Leu Leu Ser Gly Ala Val Gly<br>              100                      105                    110 | 336 |
| tct ggg act tgt gcg gct gca ggg acg gct ggt ggc act tct ctt aac<br>Ser Gly Thr Cys Ala Ala Ala Gly Thr Ala Gly Gly Thr Ser Leu Asn<br>            115                      120                    125 | 384 |
| act caa agc act tgc acc gtt gcg ggc tat tac tgg ctc cct agc ttg<br>Thr Gln Ser Thr Cys Thr Val Ala Gly Tyr Tyr Trp Leu Pro Ser Leu<br>130                         135                       140 | 432 |
| act gac agg att tta agc acg atc ggc agc cag act aac tac ggc acg<br>Thr Asp Arg Ile Leu Ser Thr Ile Gly Ser Gln Thr Asn Tyr Gly Thr<br>145                       150                     155                   160 | 480 |
| aac acc aat ttc ccc aac atg caa caa cag ctc acc tac ttg aat gcg<br>Asn Thr Asn Phe Pro Asn Met Gln Gln Gln Leu Thr Tyr Leu Asn Ala<br>                  165                      170                    175 | 528 |
| ggg aat gtg ttt ttt aat gcg atg aat aag gct tta gag aat aag aat<br>Gly Asn Val Phe Phe Asn Ala Met Asn Lys Ala Leu Glu Asn Lys Asn<br>            180                      185                    190 | 576 |
| gga act agt agt gct agt gga act agt ggt gcg act ggt tca gat ggt<br>Gly Thr Ser Ser Ala Ser Gly Thr Ser Gly Ala Thr Gly Ser Asp Gly<br>            195                      200                    205 | 624 |
| caa act tac tcc aca caa gct atc caa tac ctt caa ggc caa caa aat<br>Gln Thr Tyr Ser Thr Gln Ala Ile Gln Tyr Leu Gln Gly Gln Gln Asn<br>210                       215                     220 | 672 |
| atc tta aat aac gca gcg aac ttg ctc aag caa gat gaa ttg ctc tta<br>Ile Leu Asn Asn Ala Ala Asn Leu Leu Lys Gln Asp Glu Leu Leu Leu<br>225                       230                     235                   240 | 720 |
| gaa gct ttc aac tct gcc gta gcc gcc aac att ggg aat aag gaa ttc<br>Glu Ala Phe Asn Ser Ala Val Ala Ala Asn Ile Gly Asn Lys Glu Phe<br>                  245                      250                    255 | 768 |
| aat tca gcc gct ttt aca ggt ttg gtg caa ggc att att gat caa tct<br>Asn Ser Ala Ala Phe Thr Gly Leu Val Gln Gly Ile Ile Asp Gln Ser<br>            260                      265                    270 | 816 |
| caa gcg gtt tat aac gag ctc act aaa aac acc att agc ggg agt gcg<br>Gln Ala Val Tyr Asn Glu Leu Thr Lys Asn Thr Ile Ser Gly Ser Ala<br>            275                      280                    285 | 864 |
| gtt att agc gct ggg ata aac tcc aac caa gct aac gct gtg caa ggg<br>Val Ile Ser Ala Gly Ile Asn Ser Asn Gln Ala Asn Ala Val Gln Gly<br>            290                      295                    300 | 912 |
| cgc gct agt cag ctc cct aac gct ctt tat aac gcg caa gta act ttg<br>Arg Ala Ser Gln Leu Pro Asn Ala Leu Tyr Asn Ala Gln Val Thr Leu<br>305                       310                     315                   320 | 960 |
| gat aaa atc aat gcg ctc aat aat caa gtg aga agc atg cct tac ttg<br>Asp Lys Ile Asn Ala Leu Asn Asn Gln Val Arg Ser Met Pro Tyr Leu<br>              325                      330                    335 | 1008 |
| ccc caa ttc aga gcc ggg aac agc cgt tca acg aat att tta aac ggg<br>Pro Gln Phe Arg Ala Gly Asn Ser Arg Ser Thr Asn Ile Leu Asn Gly | 1056 |

```
                340                 345                 350
ttt tac acc aaa ata ggc tat aag caa ttc ttc ggg aag aaa agg aat    1104
Phe Tyr Thr Lys Ile Gly Tyr Lys Gln Phe Phe Gly Lys Lys Arg Asn
            355                 360                 365 atc ggt ttg cgc tat tat ggt ttc ttt tct tat aac gga gcg agc gtg    1152
Ile Gly Leu Arg Tyr Tyr Gly Phe Phe Ser Tyr Asn Gly Ala Ser Val
        370                 375                 380 ggc ttt aga tcc act caa aat aat gta ggg tta tac act tat ggg gtg    1200
Gly Phe Arg Ser Thr Gln Asn Asn Val Gly Leu Tyr Thr Tyr Gly Val
385                 390                 395                 400 ggg act gat gtg ttg tat aac atc ttt agc cgc tcc tat caa aac cgc    1248
Gly Thr Asp Val Leu Tyr Asn Ile Phe Ser Arg Ser Tyr Gln Asn Arg
                405                 410                 415 tct gtg gat atg ggc ttt ttt agc ggt atc caa tta gcc ggt gag acc    1296
Ser Val Asp Met Gly Phe Phe Ser Gly Ile Gln Leu Ala Gly Glu Thr
            420                 425                 430 ttc caa tcc acg ctc aga gat gac ccc aat gtg aaa ttg cat ggg aaa    1344
Phe Gln Ser Thr Leu Arg Asp Asp Pro Asn Val Lys Leu His Gly Lys
        435                 440                 445 atc aat aac acg cac ttc cag ttc ctc ttt gac ttc ggt atg agg atg    1392
Ile Asn Asn Thr His Phe Gln Phe Leu Phe Asp Phe Gly Met Arg Met
    450                 455                 460 aac ttc ggt aag ttg gac ggg aaa tcc aac cgc cac aac cag cac acg    1440
Asn Phe Gly Lys Leu Asp Gly Lys Ser Asn Arg His Asn Gln His Thr
465                 470                 475                 480 gtg gaa ttt ggc gta gtg gtg cct acg att tat aac act tat tac aaa    1488
Val Glu Phe Gly Val Val Val Pro Thr Ile Tyr Asn Thr Tyr Tyr Lys
                485                 490                 495 tca gca ggg act acc gtg aag tat ttc cgt cct tat agc gtt tat tgg    1536
Ser Ala Gly Thr Thr Val Lys Tyr Phe Arg Pro Tyr Ser Val Tyr Trp
            500                 505                 510 tct tat ggg tat tca ttc taa                                        1557
Ser Tyr Gly Tyr Ser Phe
        515

<210> SEQ ID NO 4
<211> LENGTH: 518
<212> TYPE: PRT
<213> ORGANISM: Helicobacter pylori

<400> SEQUENCE: 4

Met Ile Lys Lys Asn Arg Thr Leu Phe Leu Ser Leu Ala Leu Cys Ala
 1               5                  10                  15

Ser Ile Ser Tyr Ala Glu Asp Asp Gly Gly Phe Phe Thr Val Gly Tyr
            20                  25                  30

Gln Leu Gly Gln Val Met Gln Asp Val Gln Asn Pro Gly Gly Ala Lys
        35                  40                  45

Ser Asp Glu Leu Ala Arg Glu Leu Asn Ala Asp Val Thr Asn Asn Ile
    50                  55                  60

Leu Asn Asn Asn Thr Gly Gly Asn Ile Ala Gly Ala Leu Ser Asn Ala
65                  70                  75                  80

Phe Ser Gln Tyr Leu Tyr Ser Leu Leu Gly Ala Tyr Pro Thr Lys Leu
                85                  90                  95

Asn Gly Ser Asp Val Ser Ala Asn Ala Leu Leu Ser Gly Ala Val Gly
            100                 105                 110

Ser Gly Thr Cys Ala Ala Ala Gly Thr Ala Gly Gly Thr Ser Leu Asn
        115                 120                 125

Thr Gln Ser Thr Cys Thr Val Ala Gly Tyr Tyr Trp Leu Pro Ser Leu
```

```
                130                 135                 140
Thr Asp Arg Ile Leu Ser Thr Ile Gly Ser Gln Thr Asn Tyr Gly Thr
145                 150                 155                 160
Asn Thr Asn Phe Pro Asn Met Gln Gln Gln Leu Thr Tyr Leu Asn Ala
                165                 170                 175
Gly Asn Val Phe Phe Asn Ala Met Asn Lys Ala Leu Glu Asn Lys Asn
                180                 185                 190
Gly Thr Ser Ser Ala Ser Gly Thr Ser Gly Ala Thr Gly Ser Asp Gly
                195                 200                 205
Gln Thr Tyr Ser Thr Gln Ala Ile Gln Tyr Leu Gln Gly Gln Gln Asn
                210                 215                 220
Ile Leu Asn Asn Ala Ala Asn Leu Leu Lys Gln Asp Glu Leu Leu Leu
225                 230                 235                 240
Glu Ala Phe Asn Ser Ala Val Ala Ala Asn Ile Gly Asn Lys Glu Phe
                245                 250                 255
Asn Ser Ala Ala Phe Thr Gly Leu Val Gln Gly Ile Ile Asp Gln Ser
                260                 265                 270
Gln Ala Val Tyr Asn Glu Leu Thr Lys Asn Thr Ile Ser Gly Ser Ala
                275                 280                 285
Val Ile Ser Ala Gly Ile Asn Ser Asn Gln Ala Asn Ala Val Gln Gly
                290                 295                 300
Arg Ala Ser Gln Leu Pro Asn Ala Leu Tyr Asn Ala Gln Val Thr Leu
305                 310                 315                 320
Asp Lys Ile Asn Ala Leu Asn Asn Gln Val Arg Ser Met Pro Tyr Leu
                325                 330                 335
Pro Gln Phe Arg Ala Gly Asn Ser Arg Ser Thr Asn Ile Leu Asn Gly
                340                 345                 350
Phe Tyr Thr Lys Ile Gly Tyr Lys Gln Phe Phe Gly Lys Lys Arg Asn
                355                 360                 365
Ile Gly Leu Arg Tyr Tyr Gly Phe Phe Ser Tyr Asn Gly Ala Ser Val
370                 375                 380
Gly Phe Arg Ser Thr Gln Asn Asn Val Gly Leu Tyr Thr Tyr Gly Val
385                 390                 395                 400
Gly Thr Asp Val Leu Tyr Asn Ile Phe Ser Arg Ser Tyr Gln Asn Arg
                405                 410                 415
Ser Val Asp Met Gly Phe Phe Ser Gly Ile Gln Leu Ala Gly Glu Thr
                420                 425                 430
Phe Gln Ser Thr Leu Arg Asp Asp Pro Asn Val Lys Leu His Gly Lys
                435                 440                 445
Ile Asn Asn Thr His Phe Gln Phe Leu Phe Asp Phe Gly Met Arg Met
450                 455                 460
Asn Phe Gly Lys Leu Asp Gly Lys Ser Asn Arg His Asn Gln His Thr
465                 470                 475                 480
Val Glu Phe Gly Val Val Val Pro Thr Ile Tyr Asn Thr Tyr Tyr Lys
                485                 490                 495
Ser Ala Gly Thr Thr Val Lys Tyr Phe Arg Pro Tyr Ser Val Tyr Trp
                500                 505                 510
Ser Tyr Gly Tyr Ser Phe
                515

<210> SEQ ID NO 5
<211> LENGTH: 15
<212> TYPE: DNA
<213> ORGANISM: Artificial Sequence
```

```
<220> FEATURE:
<223> OTHER INFORMATION: Description of Artificial Sequence: synthetic

<400> SEQUENCE: 5
gtagtggtgg tggtg                                                    15
```